(12) United States Patent
Phillips et al.

(10) Patent No.: US 6,452,049 B1
(45) Date of Patent: *Sep. 17, 2002

(54) RECOVERING NITRAMINES AND REFORMULATION OF BY-PRODUCTS

(75) Inventors: Randall S. Phillips, Carson City, NV (US); Andrew W. Cain, Rio Rancho, NM (US); Thomas J. Schilling, Albuquerque, NM (US); Michael W. Miks, Albuquerque, NM (US)

(73) Assignee: TPL, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/571,748

(22) Filed: May 15, 2000

Related U.S. Application Data

(63) Continuation of application No. 09/212,050, filed on Dec. 15, 1998, now Pat. No. 6,063,960.
(60) Provisional application No. 60/069,492, filed on Dec. 15, 1997.

(51) Int. Cl.⁷ ............................................... C07C 24/00
(52) U.S. Cl. ..................................................... 564/112
(58) Field of Search ........................................ 564/112

(56) References Cited

U.S. PATENT DOCUMENTS 4,098,627 A    7/1978   Tompa et al.
4,389,265 A    6/1983   Tompa et al.
5,523,517 A    6/1996   Cannizzo

OTHER PUBLICATIONS

Leake, E.E., *Recovery of HMX From Scrap PBX–9404 High Explosive*, Oct. 26, 1973, Mason & Hangar–Silas Mason Co., Inc., Burlington, Iowa.

Phillips, R.S., et al., "Demilitarization of Energetic Materials and Recovery of Value–Added Products", May 6–8, 1997, TPL, Inc., Albuquerque, NM.

Schilling, T.J., et al, "Value Added Products from the Demilitarization of Energetic Materials", *Life Cycles of Energetic Materials, Proceedings, 1994 Conference*, Dec 11–16, 1994, pp. 337–346, Del Mar, CA.

Tompa, A.S., et al., "Propellant Ingredient Reclamation by Solvolysis*", *1974 Jannaf Propulsion Meeting*, Oct. 22–24, 1974, pp. 737–755, vol. 1, Part II, Chemical Propulsion Information Agency, Silver Spring, MD.

"Utilization and Disposal of Solid Propellant and Explosives Wastes", NSWC/WOL TR 77–72, 1977, p. 4 (Introduction to Appendix).

Primary Examiner—Paul J. Killos
(74) Attorney, Agent, or Firm—Jeffrey D. Myers; Deborah A. Peacock

(57) ABSTRACT

Methods to recover nitramines from energetic materials yielding useable by-products and producing zero waste. The methods are used on materials containing HMX and RDX.

28 Claims, No Drawings

RECOVERING NITRAMINES AND REFORMULATION OF BY-PRODUCTS

CROSS-REFERENCE TO RELATED APPLICATIONS

This application claims the benefit of the filing of U.S. Provisional Patent Application Serial No. 60/069,492, entitled METHOD FOR RECOVERING NITROAMINES AND REFORMULATION OF BY-PRODUCTS, filed on Dec. 15, 1997, and is a continuation of U.S. application Ser. No. 09/212,050, entitled RECOVERING NITROAMINES AND REFORMULATION OF BY-PRODUCTS, filed Dec. 15, 1998, to issue as U.S. Pat. No. 6,063,960 on May 16, 2000 and the specification thereof is incorporated herein by reference.

GOVERNMENT RIGHTS

The U.S. Government has a paid-up license in this invention and the right in limited circumstances to require the patent owner to license others on reasonable terms as provided for by the terms of Contract No. NO0164-95-C-0023 awarded by U.S. Department of Defense.

BACKGROUND OF THE INVENTION

1. Field of the Invention (Technical Field)

The present invention relates to the recovery of nitramines from surplus energetic materials, and their reformulation into useful products.

2. Background Art

The U.S. military has stockpiled thousands of tons of surplus energetic materials that are now obsolete and either will not or cannot be used for future applications. Reduction of this obsolete surplus is of economic and environmental necessity. However, the traditional means of open burning, open detonation or dumping are not acceptable. They yield no useable materials, contribute to pollution and increase disposal site remediation costs. Two of the major components in many of these energetic materials are cyclotetramethylene tetranitramine (HMX) and cyclotetramethylene trinitramine (RDX). These compounds have the potential to be recovered from the energetic material surplus in a demilitarization method, and used as blasting agents that are booster-sensitive but not blasting cap-sensitive, nutrient additives for fertilizer, explosive metal bonding, and used in well perforating charges. On an economic basis, demilitarization to produce purified nitramines is preferable to mere reuse as blasting agents—gross income from the sale of the processed HMX is on the order of a magnitude greater than that from the sale of the surplus for reuse as is.

Various chemical demilitarization methods have been proposed, but involve the use of organic solvents which result in hazardous waste. For example, U.S. Pat. No. 5,523,517, entitled Destruction of Nitramines Employing Aqueous Dispersion of Metal Powders to Cannizzo et. al. uses metal salts, which must be separated and properly disposed of, and U.S. Pat. No. 4,098,627, entitled Solvolytic Degradation of Pyrotechnic Materials Containing Crosslinked Polymers to Tompa et. al. uses hazardous solvents such as ethylene diamine, benzene and DMSO (dimethylsulfoxide). Neither addresses the need for producing reusable products from the demilitarization.

The continuously mounting stockpile emphasizes the need for a more cost-effective method that maintains quality of product. The cost-effectiveness depends upon capital investment (equipment), supplies, waste clean-up required, and labor. With the present need for a process that has no environmental repercussions, a method to demilitarize surplus energetic materials that results in a useable resource and yet has a zero waste stream is most advantageous. The present invention addresses this need.

SUMMARY OF THE INVENTION
(DISCLOSURE OF THE INVENTION)

The present invention is directed to a method of recovering nitramines from energetic materials and yielding an additional useful product. The preferred method comprising the steps of solubilizing the material in a nitric acid solution, removing the effluent to yield a nitramine, neutralizing the effluent with a base, removing the liquid content from the effluent to yield a compound salt, rinsing the nitramine, and desensitizing the nitramine.

The nitric acid solution is preferably 60–70% nitric acid, and more preferably 65–70% nitric acid. The steps of solubilizing and stirring are preferably conducted at ambient temperature. After solubilization, the solution may be heated, preferably to a temperature between 40–80° C., and more preferably to at least 70° C. The effluent is removed preferably by centrifuging or filtering. The effluent is preferably neutralized with ammonium hydroxide, and more preferably with at least 26% ammonium hydroxide, to neutralize preferably to a pH of approximately 6.8. The compound salt yielded from evaporation is preferably ammonium nitrate polymeric fuel (ANPF).

The nitramine is preferably rinsed with water, and desensitized preferably with alcohol, and more preferably isopropyl alcohol, added to a total liquid content of 20 w %. The method preferably yields cyclotetramethylene tetranitramine.

The invention is also directed to a method of recovering nitramines from energetic materials comprising providing an energetic material, forming a solution, adding a substance to increase density of the solution, and separating the solution into a wax component and a nitramine-containing component.

In the preferred embodiment, the energetic material provided is a compound containing a nitramine, and preferably cyclotetramethylene trinitramine. The solution is formed preferably by adding water, preferably to form a water to material ratio of between 3:1 and 7:1, and more preferably of at least 5:1. The substance added to increase density is preferably a salt, and more preferably $CACl_2$. The substance may also be sodium chloride, sodium bicarbonate, potassium nitrate or a sulfate. The density is increased to between 1.1 and 1.7 g/cc, and preferably to approximately 1.2 g/cc. The solution may be heated, preferably to 80–85° C. A surfactant may be added. The surfactant added is preferably resistant to high temperatures and high acidity, and is more preferably Tween 20. The solution is preferably cooled to a maximum of 70° C. A preferred embodiment of the invention involves separation by skimming the wax substance from the top of the solution, and aspirating the solution to leave the nitramine. The product left after aspiration is preferably cyclotetramethylene trinitramine, which is then preferably rinsed.

A primary object of the present invention is to provide a method for demilitarization of surplus energetic materials that generates value-added products.

Another object of the present invention is to provide a method for demilitarization that results in a zero waste stream.

Another object of the present invention is to provide a method for demilitarization that is less costly.

Another object of the present invention is to provide a method of demilitarization that addresses the need of a diverse surplus industry.

Another object of the present invention is to provide a method of demilitarization that relies upon disparate densities for separation of compounds.

A primary advantage of the present invention is the lack of hazardous waste of which to dispose.

Another advantage of the present invention is the use of inexpensive and readily available resources in the demilitarization process.

Another advantage of the present invention is the production of value-added products of high quality.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENTS (BEST MODES FOR CARRYING OUT THE INVENTION)

The present invention is a demilitarization method of recovering nitramines, particularly HMX (cyclotetramethylene tetranitramine) and RDX (cyclotetramethylene trinitramine) from energetic materials. The energetic materials include HMX-containing compounds such as LX-14, VTG-5A, and WAY, and RDX-containing compounds such as Comp-A3. The method comprises the following steps: The energetic material is solubilized in a nitric acid solution. This solution is preferably 60–70% nitric acid, and more preferably 65–70% nitric acid. A preferred solvent to feed ratio was 0.5:1 l/kg, and a most preferred ratio is 1.0:1.0. The solubilization can take place at ambient temperature. The mixture is then heated to between 40–80° C., and preferably to approximately 70° C. The heat is needed to recover the HMX from the slurry, and further solubilize the oxidized binder and completely remove it from the HMX. If heat is added at the beginning, the processing time is decreased. However, the longer the heating time, the more nitric acid required.

After heating, the solution is either centrifuged or filtered to remove the effluent. The remaining substance is a nitramine, with particle size and morphology unaffected.

The resulting particles are round. Rounded particles are important for reuse applications—they blend readily, and have less sensitivity to shock and mechanical stimuli.

The nitramine is rinsed, preferably with water to minimize waste, and then is desensitized with an alcohol, preferably isopropyl alcohol, to prepare for shipping or storage. The alcohol content should bring the nitramine to a total liquid content of 20% by weight.

The effluent that is removed from the nitramines is neutralized with 26–30% ammonium hydroxide to a pH of approximately 6.8. The water content is evaporated off, and the remaining compound is ANPF (ammonium nitrate polymeric fuel), a useable by-product.

Another method for recovering nitramine form energetic materials involves extraction of RDX from RDX-containing compounds. The method relies upon disparate densities of the binder and RDX to accomplish the separation. The method comprises adding water to the energetic material to form a solution. The water to material ratio should be from 3:1 to 7:1, and preferably be 5:1 by weight.

The density of the solution is then increased to between 1.1–1.7, and preferably to approximately 1.2, by the addition of a salt. This salt is preferably calcium chloride due to its ease of disposability. However, the salt may also be sodium chloride, sodium bicarbonate, potassium nitrate, or a sulfate. The increased density allows for the wax to separate from the nitramine physically—the nitramine has a heavier density and sinks, while the wax has a lighter density and floats. The solution is heated to between 80–85° C. in the presence of a surfactant that can withstand high temperatures and an acid environment, such as Tween 20™ (ICI Americas, Inc, Edinburgh, Scotland). The surfactant facilitates the heat transfer to the wax. The solution is then cooled to a temperature at or below 70° C. to coagulate the wax at the surface. The wax is then skimmed off the top, and the solution is aspirated to leave the nitramine. The nitramine is rinsed to purify.

Industrial Applicability

The invention is further illustrated by the following non-limiting examples.

EXAMPLE 1

A preferred embodiment of the HMX-compound demilitarization process is as follows: The materials that are used in the process are technical grade nitric acid (preferably 60–70% by weight, and more preferably 65–70% by weight), and ammonium hydroxide (preferably 26–30% by weight). Any less than 60% by weight nitric acid yields HMX that is yellow in color, indicating the presence of binder. The water was non-purified, and filtered through a 40 micron filter. The rinse acid from the process was used as a reaction acid for a second process, thus reducing costs. The process is neither labor- nor time-intensive.

The plastic binder of the surplus energetic material was solubilized in 65–70% nitric acid at ambient temperature and pressure. The solvent to feed ratio was 1:1. Degradation was finalized by agitating and heating the mixture to approximately 70° C. The mixture was then centrifuged to remove the effluent, which was then neutralized with 26–30% ammonium hydroxide to form ammonium nitrate. The water was evaporated to yield approximately 98% ammonium nitrate plus 2% degraded polymer residue (plastic binder) plus trace HMX, a compound salt called ANPF (ammonium nitrate polymeric fuel). This ANPF had a tested detonation velocity of an average of 2.4 km/sec, and in fertilization tests on *Brassica rapa,* it yielded plants with higher than average weights with on adverse growth effects.

The recovered HMX was rinsed with water to remove the nitric acid, then centrifuged. Per kg of LX-14, for example a maximum of 15–20 liters of water was needed to remove acidity. The rinse water was added to effluent before the neutralization step. Isopropyl alcohol was added to the resulting HMX to a total liquid content of 20% by weight to desensitize the HMX for storage or transport, and prevent freezing. The HMX product recovered from this method was primarily class I, and 8–10% class 5 HMX as defined in HMX Military Specification MIL-H-4544B, and was relatively pure, as evidenced by its white color.

EXAMPLE 2

For energetic materials containing RDX (e.g., Comp A-3) encapsulated in a wax binder, the method of nitramine extraction was slightly different, but still produced a relatively pure product without hazardous waste.

Comp A-3 was added to water in a water to feedstock ratio of 5:1 (mass). $CaCl_2$ was added to increase the density of the solution from 1.0 g/cc to 1.2 g/cc. The temperature of the mixture was increased to 80–85° C. A surfactant (e.g., 5 % by weight Tween 20™, ICI Americas, Inc, Edinburg, Scotland) was added to facilitate the heat transfer from the heated solution to the wax. The resulting density change caused the physical separation of the wax and the RDX as they uncoupled. Because the density of wax is less than 1.2 g/cc, it floated to the surface. Likewise, because the density of RDX is greater than 1.2 g/cc, once separated from the binder, it sank to the bottom of the reaction vessel. The reaction mixture was cooled to approximately 70° C. to minimize the amount of wax in solution. The wax was then skimmed off the surface, and the solution layer was aspirated. The remaining RDX was rinsed, centrifuged, and packaged for storage.

Several tests were run to determine quality of the extracted HMX and ANPF (ammonium nitrate polymeric fuel). Scanning electron micrographs (SEM) showed a morphology of HMX with no jagged edges. The chemical purities were established by Fourier transform infrared spectroscopy (FT-IR) and further characterized by proton nuclear magnetic resonance spectroscopy (NMR-IBM Instruments Inc., model NR/300 FT NMR). Purity was confirmed using differential scanning calorimetric (DSC) melting tests. HPLC (high performance liquid chromatography) was conducted to determine content and purity, as well, using a Brownlee reverse phase, 5 $\mu$C-18 column with mobile phase of 50% water:50% acrilonitrile at 40° C., 0.7 ml/min flow, with a 20 $\mu$l sample, UV at 220 nm.

EXAMPLE 3

Recovery for HMX in VTG-5A was performed as follows: The recovery for VTG-5A utilized the basic nitric acid process that was developed for LX-14, with modifications as needed. The composition was:

| | |
|---|---|
| HMX | 40.50% |
| Nitroglycerin (NG) | 21.32% |
| Aluminum (Al) | 19.50% |
| Ammonium perchlorate (AP) | 10.00% |
| Polyglycoladipate (S-1011-35) | 6.54% |
| Liquid aliphatic isocyanate (N-100) | 1.04% |
| N-methyl p-nitroaniline (MNA) | 0.62% |
| 2-Nitrodiphenylamine (2-NDPA) | 0.22% |
| Nitrocellulose (NC) | 0.20% |
| Hexamethylene diisocyanate (HDI) | 0.06% |

HMX was recovered from VTG-5A using 70% technical grade nitric acid. Passive extractions with ambient temperature acid and stirred extractions with near boiling acid were performed. The passive extractions at ambient temperature indicated that after a 24 hour period, the binder was oxidized, degraded, and solubilized. The aluminum and the HMX remained as solids in the nitric acid. Upon heating, the aluminum went into solution and the HMX remained. The recovered HMX was white. The stirred reactions with near boiling (70° C.) nitric acid showed that the binder dissolved/degraded and the HMX partially dissolved in the nitric acid at 70° C. To recover the HMX, the acid solution was added to water and the HMX crash precipitated out of solution. The recovered HMX was white.

Lab scale efforts recovered a total of 250 grams HMX from VTG-5A with single batches recovering up to 40 grams HMX. HPLX analysis for the recovered HMX from VTG-5A indicated that the material was 99.9% HMX. Capillary melting points for the recovered HMX from VTG-5A were 277° C. The melting point for HMX standard is 278–280° C. The recovered HMX was found to be very pure.

EXAMPLE 4

Recovery for HMX in WAY was performed as follows: The composition for WAY is classified, but is believed to be similar to VTG-5A. HMX was recovered from WAY using 70% nitric acid. Passive extractions with ambient temperature indicated that after a 24 hour period, the binder was degraded/solubilized. The aluminum and the HMX remained as solids in the nitric acid. Upon heating, the aluminum dissolved and the HMX remained. The recovered HMX was white. The stirred reactions with near boiling (70° C.) nitric acid showed that the binder dissolved/degraded, the aluminum dissolved and the HMX partially dissolved in the nitric acid at 70° C. To recover the HMX, the acid solution was added to water and the HMX crash precipitated out of solution. The recovered HMX was white.

Lab scale efforts recovered a total of 50 grams HMX from WAY, with single batches recovering up to 10 grams HMX. HPLC analysis for the recovered HMX from WAY indicated that the material was 99.9% HMX. Capillary melting points for the recovered HMX from WAY were 277° C. The melting point for HMX standard is 278–280° C. The recovered HMX was found to be very pure.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of recovering or reprocessing nitramines from energetic materials comprising the following steps:
    a) providing energetic material;
    b) solubilizing the material in an acid solution;
    c) removing an effluent from the solution to leave a nitramine; and
    d) neutralizing the effluent.

2. The method of claim 1 wherein the step of solubilizing the material comprises solubilizing in a nitric acid solution.

3. The method of claim 2 wherein the step of solubilizing the material comprises solubilizing in less than or equal to 70% nitric acid solution.

4. The method of claim 3 wherein the step of solubilizing the material comprises solubilizing in a 60–70% nitric acid solution.

5. The method of claim 1 wherein the neutralizing step comprises neutralizing the effluent with a base.

6. The method of claim 5 wherein the neutralizing step comprises neutralizing with ammonium hydroxide.

7. The method of claim 6 wherein the neutralizing step comprises neutralizing with at least approximately 26% ammonium hydroxide.

8. The method of claim 6 wherein the neutralizing step comprises neutralizing the solution to a pH of approximately 6.8.

9. The method of claim 1 additionally comprising the step of removing liquid content from the effluent.

10. The method of claim 9 wherein the removing step comprises removing liquid content from the effluent to yield a compound salt.

11. The method of claim 9 wherein the step of removing liquid content comprises evaporating to yield ammonium nitrate polymeric fuel (ANPF).

12. The method of claim 1 additionally comprising the step of rinsing the nitramine.

13. The method of claim 12 wherein the step of rinsing the nitramine comprises rinsing with an aqueous solution.

14. The method of claim 1 additionally comprising the step of desensitizing the nitramine.

15. The method of claim 14 wherein the step of desensitizing the nitramine comprises desensitizing by adding alcohol.

16. The method of claim 15 wherein the step of desensitizing the nitramine by adding alcohol comprises desensitizing by adding isopropyl alcohol to a total liquid content of approximately 20% by weight.

17. The method of claim 1 wherein the step of solubilizing the material comprises solubilizing a nitramine.

18. The method of claim 1 additionally comprising after step (b) the step of agitating the solution.

19. The method of claim 1 further comprising after step (b) the step of heating the solution.

20. The method of claim 19 wherein the step of heating comprises heating to between approximately 40° C. and 80° C.

21. The method of claim 19 wherein the step of heating comprises heating to at least approximately 70° C.

22. The method of claim 1 wherein steps (b) and (c) are conducted at approximately ambient temperature.

23. The method of claim 1 wherein the step of removing the effluent comprises at least one method selected from the group consisting of centrifuging and filtering.

24. The method of claim 1 wherein the step of removing the effluent to leave a nitramine comprises removing the effluent to leave a cyclotetramethylene tetranitramine.

25. The method of claim 1 wherein the energetic material comprises a propellant material.

26. The method of claim 1 wherein the energetic comprises an explosive material.

27. A method of recovering or reprocessing nitramines from energetic materials comprising the following steps:
 a) solubilizing the material in an acid solution;
 b) removing an effluent from the solution to leave a nitramine;
 c) neutralizing the effluent;
 d) removing liquid content from the effluent to yield a compound salt;
 e) rinsing the nitramine; and
 f) desensitizing the nitramine.

28. A method of recovering or reprocessing nitramines from energetic materials comprising the following steps:
 a) providing the energetic material;
 b) forming a solution;
 c) adding a substance to the solution to increase density; and
 d) separating the solution into a wax component and a nitramine-containing component.

* * * * *